(12) United States Patent
Murahari et al.

(10) Patent No.: US 9,782,509 B2
(45) Date of Patent: Oct. 10, 2017

(54) IN-WALL ROOM FRESHENER MODULES AND RELATED DEVICES AND SYSTEMS

(71) Applicant: Eaton Corporation, Cleveland, OH (US)

(72) Inventors: Saivaraprasad Murahari, Peachtree City, GA (US); Pramod Kumar, Peachtree City, GA (US)

(73) Assignee: Eaton Corporation, Cleveland, OH (US)

( * ) Notice: Subject to any disclaimer, the term of this patent is extended or adjusted under 35 U.S.C. 154(b) by 0 days.

(21) Appl. No.: 14/715,886

(22) Filed: May 19, 2015

(65) Prior Publication Data

US 2016/0339134 A1 Nov. 24, 2016

(51) Int. Cl.
*A61L 9/14* (2006.01)
*B05B 11/00* (2006.01)
(Continued)

(52) U.S. Cl.
CPC ............ *A61L 9/14* (2013.01); *B05B 11/3052* (2013.01); *B05B 12/08* (2013.01);
(Continued)

(58) Field of Classification Search
CPC .......... A61L 9/00; A61L 9/12; A61L 2209/00; A61L 2209/10–2209/12; A61L 2209/133;
(Continued)

(56) References Cited

U.S. PATENT DOCUMENTS 3,228,609 A * 1/1966 Edelstein ............. B65D 83/262
 222/162
5,231,796 A * 8/1993 Sims ........................ E04B 1/72
 43/124

(Continued)

FOREIGN PATENT DOCUMENTS

FR 2 647 018 A1 11/1990
WO WO 2006/130410 A2 12/2006
(Continued)

OTHER PUBLICATIONS

Persaud et al., Analysis of discrimination mechanisms in the mammalian olfactory system using a model nose, Nature, 1982, pp. 352-355, vol. 299.

(Continued)

*Primary Examiner* — Paul R Durand
*Assistant Examiner* — Andrew P Bainbridge
(74) *Attorney, Agent, or Firm* — Myers Bigel, P.A.

(57) ABSTRACT

In-wall dispensing modules, such as room freshener modules, can reside in a housing with a cover that can be opened to access an interior space of the module to, inter alia, replace used containers. The housings are configured to reside inside a wall of a room. The front cover can be a planar cover that is flush, slightly recessed or slightly protrudes from the wall. The housings can be a "custom" housing size and/or may be configured to occupy a single gang box or a compartment of a multi-gang junction box. The modules can include an actuator that can cause a canister to emit scented fluid at desired intervals and/or (Continued)

on-demand. The modules can have a User Interface (UI) wireless and/or wired connection to a whole-house "smart" system.

24 Claims, 11 Drawing Sheets

(51) Int. Cl.
| | |
|---|---|
| *B05B 12/08* | (2006.01) |
| *G04C 23/38* | (2006.01) |
| *B65D 83/14* | (2006.01) |
| *B65D 83/38* | (2006.01) |
| *G04C 23/48* | (2006.01) |
| *G04C 23/04* | (2006.01) |
| *B05B 15/06* | (2006.01) |
| *B05B 12/02* | (2006.01) |

(52) U.S. Cl.
CPC .... *A61L 2209/111* (2013.01); *A61L 2209/133* (2013.01); *B05B 12/02* (2013.01); *B05B 15/06* (2013.01); *B65D 83/14* (2013.01); *B65D 83/388* (2013.01); *G04C 23/04* (2013.01); *G04C 23/38* (2013.01); *G04C 23/48* (2013.01)

(58) Field of Classification Search
CPC .......... A61L 9/03; A61L 9/14; A61L 2209/15; B67D 3/00; B67D 7/08; B65D 83/14; B65D 83/52; B65D 83/525; B65D 83/205–83/206; B65D 83/26; B65D 83/262; B65D 83/265; B65D 83/267; B65D 83/38; B65D 83/388; B05B 1/3033; B05B 3/00; B05B 15/06; B05B 1/3053; B05B 12/02; B05B 12/08; B05B 11/3052; G04C 23/38; G04C 23/40; G04C 23/42; G04C 23/44; G04C 23/46; G04C 23/48; G04C 23/50; G04C 23/02; G04C 23/04
USPC ..... 222/28, 36–38, 642–649, 161, 173, 612, 222/180, 182, 183, 181.3, 192; 239/273–285; 422/4–5, 105, 116, 422/123–126, 120, 305–306; 43/132.1
See application file for complete search history.

(56) References Cited

U.S. PATENT DOCUMENTS

| | | | | |
|---|---|---|---|---|
| 5,531,344 | A * | 7/1996 | Winner | B65D 83/262 222/1 |
| 5,673,825 | A | 10/1997 | Chen | |
| 5,788,569 | A | 8/1998 | Lee | |
| 6,039,212 | A * | 3/2000 | Singh | B65D 83/262 222/30 |
| 6,267,297 | B1 * | 7/2001 | Contadini | A61L 9/12 222/646 |
| 6,708,444 | B2 * | 3/2004 | Aesch, Jr. | A01M 1/245 43/124 |
| 7,350,720 | B2 * | 4/2008 | Jaworski | A61L 9/03 239/34 |
| 8,607,888 | B2 * | 12/2013 | Nusbaum | A62C 35/023 169/74 |
| 2002/0051739 | A1 * | 5/2002 | Wang | A61L 2/202 422/105 |
| 2003/0124022 | A1 * | 7/2003 | Georges | A61L 9/03 422/5 |
| 2007/0102456 | A1 * | 5/2007 | Tsay | A61L 9/14 222/321.8 |
| 2007/0199952 | A1 * | 8/2007 | Carpenter | A61L 9/14 222/52 |
| 2008/0179073 | A1 * | 7/2008 | Drane | H01H 21/085 174/67 |
| 2010/0059602 | A1 * | 3/2010 | Chiou | A01M 1/2038 239/70 |
| 2010/0096409 | A1 * | 4/2010 | Wainwright | A01M 1/2038 222/181.2 |
| 2011/0295434 | A1 * | 12/2011 | Luc | A61L 9/035 700/283 |
| 2016/0339134 | A1 * | 11/2016 | Murahari | A61L 9/14 |

FOREIGN PATENT DOCUMENTS

| | | |
|---|---|---|
| WO | WO 2008/115391 A2 | 9/2008 |
| WO | WO 2013/043696 A2 | 3/2013 |

OTHER PUBLICATIONS

International Search Report and the Written Opinion of the International Searching Authority corresponding to International Patent Application No. PCT/US2016/033169 (29 pages) (dated Nov. 18, 2016).

* cited by examiner

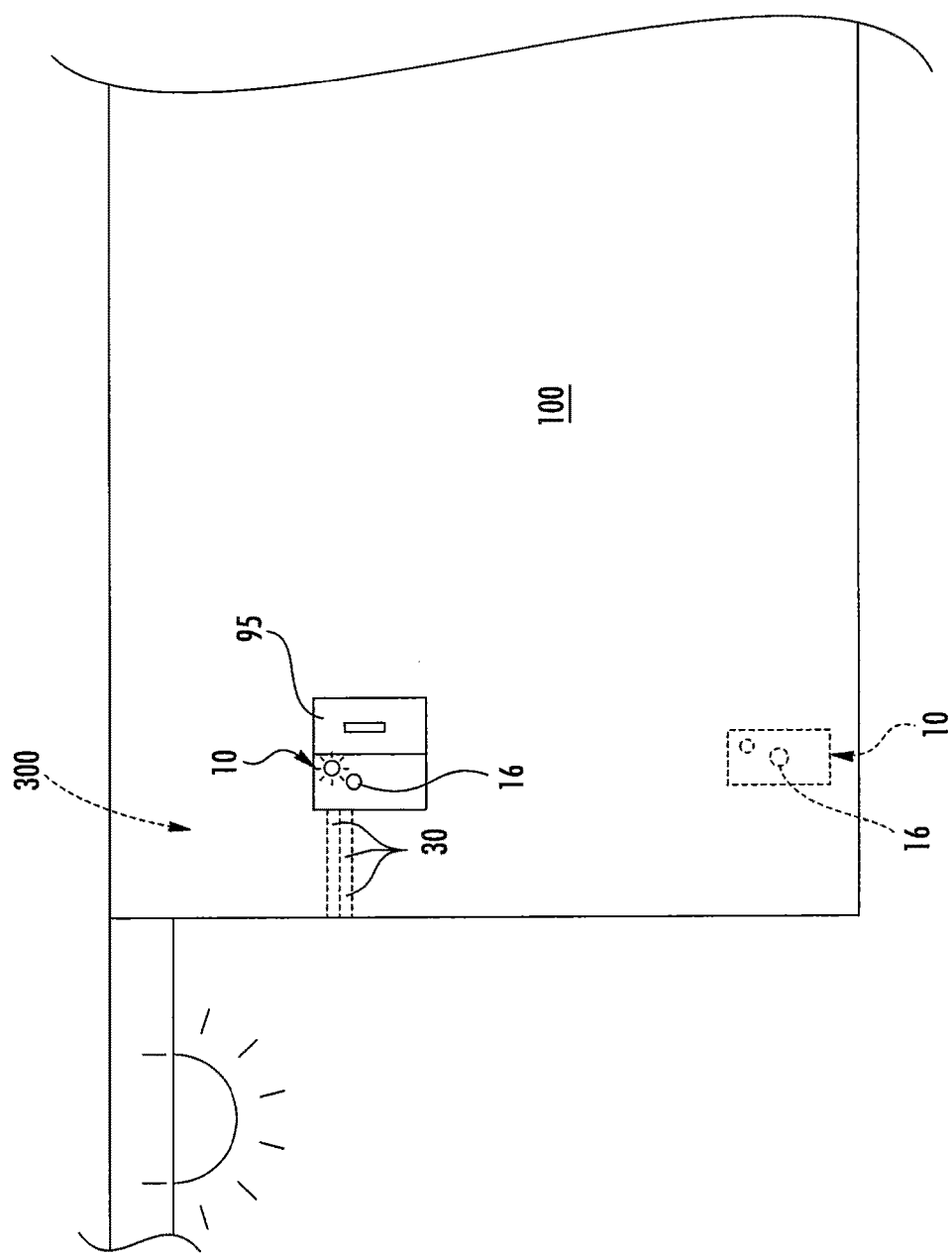

IN-WALL ROOM FRESHENER MODULES AND RELATED DEVICES AND SYSTEMS

FIELD OF THE INVENTION

The present invention relates to room dispensing units such as room fresheners.

BACKGROUND OF THE INVENTION

There are many room fresheners and dispensing devices on the market including those that need to be plugged into an outlet. These types of devices occupy an electrical outlet and may be visually unappealing.

SUMMARY OF EMBODIMENTS OF THE INVENTION

Embodiments of the present invention are directed to in-wall dispensing modules, such as, for example, room freshener modules.

Embodiments of the invention are directed to in-wall room freshener modules that reside in a housing with a cover that can be opened to access an interior space of the modules to, inter alia, replace used room freshener containers. The housings can be configured to reside behind a wall of a room. The front cover can be a planar cover that is flush, slightly recessed or that slightly protrudes from the wall. The housings can be a "custom" housing size and/or may be configured to occupy a single gang junction or mounting box or a compartment of a multi-gang junction or mounting box.

The modules can include an actuator that can cause a canister to emit air freshener at desired intervals and/or on-demand.

The modules can have a User Interface (UI) and may have a wireless and/or be wired connection to a whole-house "smart" control system.

Embodiments of the present invention are directed to modules that include a housing with an interior cavity. The housing is sized and configured to reside internal to a wall. The modules also include a front cover attached to the housing. The front cover has at least one open port extending therethrough. The front cover can be opened and closed for access to the interior cavity when the housing is mounted in the wall. The module can also include at least one sensor and/or detector held by or in the housing configured to detect at least one of: whether a container is in position in the housing, whether the cover is closed, whether content of a container held in the housing is low, and whether an external object is in proximity to the front cover. The module can also include a controller residing in the cavity of the housing. The controller is in communication with the at least one sensor and is configured to dispense a substance from a container held in the housing.

The front cover can include a user interface (UI) that allows a user to interact with the controller to adjust and/or set a dispensing schedule of a container held in the housing and an externally visible indicator light in communication with the controller.

The module can include a container with a spray nozzle held in the housing, and an actuator held in the housing. The actuator can be configured to cause the nozzle to spray the substance through the open port in the front cover.

The module can include a container of room freshener held in a canister with a spray nozzle. The nozzle can be configured to spray room freshener through the at least one port in the door of the front cover.

The housing can include a container support system in the cavity. The container support system can include spaced apart vertically stacked rails that hold a support member to place a container at a desired vertical height in the cavity.

The support member can have a planar upper surface portion bounded by laterally spaced apart first and second upwardly extending sides on opposing sides thereof.

The housing can be sized and configured to reside in a single gang box, a custom size gang box, or in a space of a standard multiple gang box.

The module can have a printed circuit board that holds the controller and a power supply. The housing can include a wall with wire ports and the wires can connect to the printed circuit board and power the power supply.

The module can include a container support system in the housing cavity that allows for x, y and z positional adjustment of a respective container in the housing cavity.

Other embodiments are directed to a room freshener module. The module includes a housing with an interior cavity. The housing is sized and configured to reside internal to a wall. The housing includes wire ports on a sidewall, rear wall, floor and/or ceiling thereof. The module includes a front cover attached to the housing. The front cover has at least one open port extending therethrough. The front cover can be opened and closed for access to the interior cavity when the housing is mounted to the wall. The front cover can be substantially flush with an external surface of the wall. The module can include at least one actuator in the housing cavity and a printed circuit board with a controller and power supply residing in the cavity. The controller can be in communication with the at least one actuator and is configured to direct the actuator to move to dispense a substance from a nozzle of a room freshener container held in the housing. The module also includes a user interface (UI) in communication with the controller that allows a user to interact with the controller to adjust and/or set a dispensing schedule.

The housing can be sized and configured to reside in a single gang box or in a space of a multiple gang box.

The module can include a container of room freshener held in the housing cavity with nozzle in alignment with the open port of the front cover.

The module can include an LED indicator light in communication with the controller and an audible alert in communication with the controller.

The housing can include wire ports on a sidewall, rear wall, floor and/or ceiling thereof, and hot, ground and neutral wires from an electrical circuit can extend therethrough to attach to the printed circuit board to power the power supply.

The controller can be in communication with a whole house control circuit that also controls other household devices such as one or more of a security alarm system, a lighting system and/or a heating and air conditioning system.

Still other embodiments are directed to systems for dispensing a substance to an environment. The systems include a housing that resides internal to a wall. The housing has a cavity closed by a front cover held so that front cover is flush or substantially flush with the wall. A front cover attached to the housing. The front cover has at least one open port extending therethrough. The front cover can be opened and closed for access to the interior cavity when the housing is mounted in the wall. The systems also include at least one actuator held in the housing and at least one sensor held in the housing. The at least one sensor is configured to detect at least one of: whether a container is in position in the housing, whether the cover is closed, or whether content of a container held in the housing is low. The systems also include a printed circuit board comprising a controller residing in the cavity of the housing. The controller can be in communication with the at least one sensor and the at least one actuator and is configured to direct the actuator to depress a nozzle of a container in the housing to dispense a substance from the container in the housing. The systems also include hot, ground and neutral wires from an electrical circuit attached to the printed circuit board to power the power supply.

The housing can be sized and configured to reside in a single gang box or in a space of a multiple gang box.

The system can include a container of room freshener held in the housing cavity with nozzle in alignment with the open port of the front cover.

The front cover can include an LED indicator light in communication with the controller. The system can also include an audible alert in communication with the controller.

The controller can be in communication with a whole house control circuit that also controls other household devices including one or more of a security alarm system, a lighting system and/or a heating and air conditioning system.

Further features, advantages and details of the present invention will be appreciated by those of ordinary skill in the art from a reading of the figures and the detailed description of the preferred embodiments that follow, such description being merely illustrative of the present invention.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 4B illustrates an optional front cover removed for illustration of an exemplary printed circuit board assembly according to embodiments of the present invention.

FIG. 9 is a schematic illustration of an in-wall dispensing module according to embodiments of the present invention.

DETAILED DESCRIPTION OF EMBODIMENTS OF THE INVENTION

Figure 1:
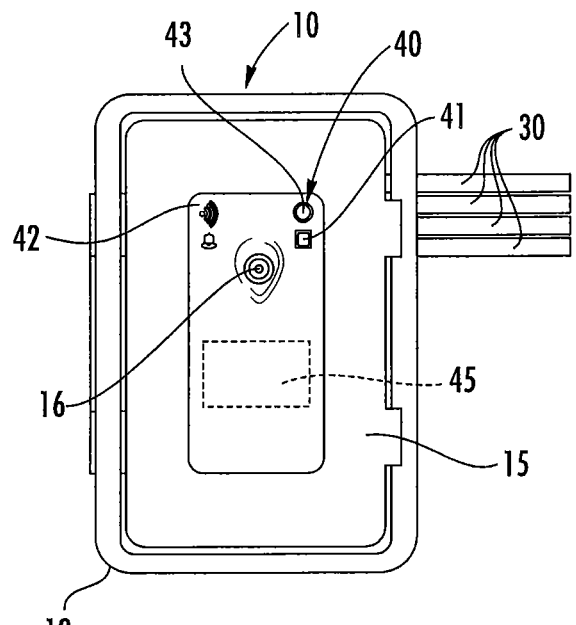
FIG. 1 is a front view of an exemplary dispensing module according to embodiments of the present invention.

The present invention now will be described more fully hereinafter with reference to the accompanying drawings, in which illustrative embodiments of the invention are shown. Like numbers refer to like elements and different embodiments of like elements can be designated using a different number of superscript indicator apostrophes (e.g., 10, 10', 10", 10'''). Abbreviated versions of the word "Figure" such as "FIG." and "FIG." are used interchangeably in the application.

In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly.

The term "about" refers to numbers in a range of +/−20% of the noted value.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

The term "controller" is used broadly and includes control circuitry in an in-wall housing holding a room freshener module and can include one or more microcontrollers, microprocessors, programmable logic controllers (PLCs), digital signal processors (DSPs), or Integrated Circuits (ICs). The ICs can optionally include at least one Application-Specific Integrated Circuits (ASICs).

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

Figure 2:
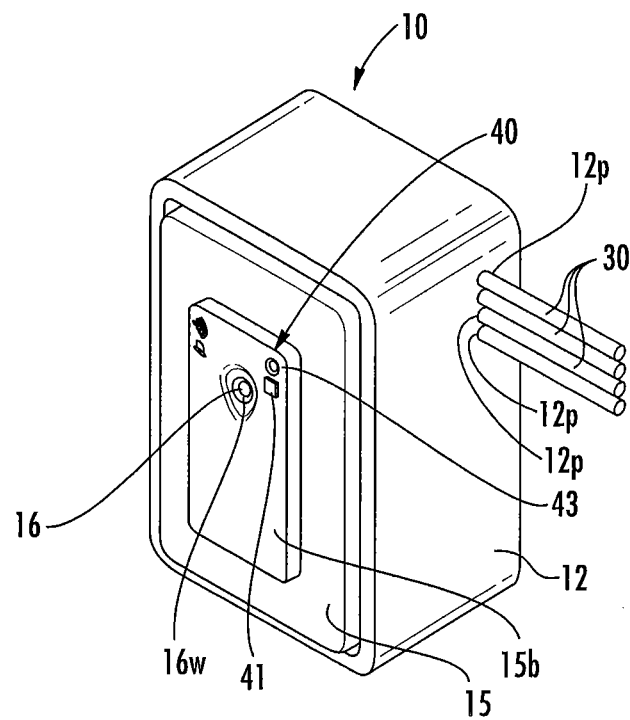
FIG. 2 is a side perspective view of the device shown in FIG. 1, according to embodiments of the present invention.
Figure 3:
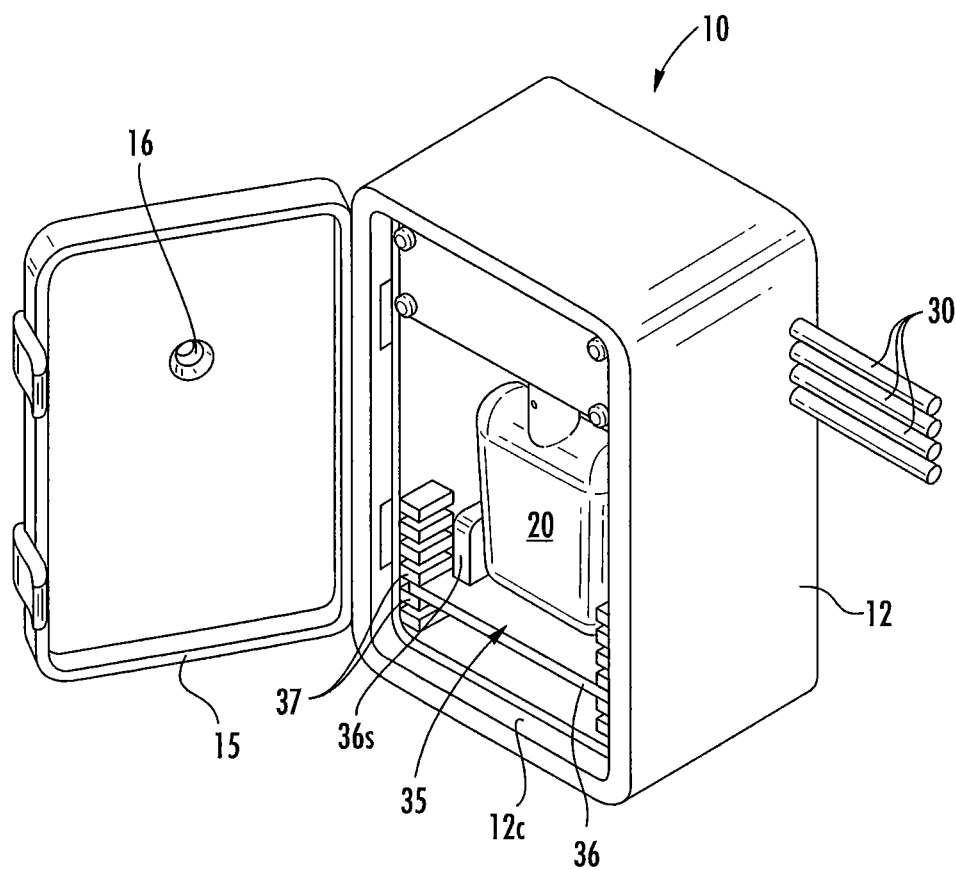
FIG. 3 is a side perspective view of the device shown in FIGS. 1 and 2 with the door open according to embodiments of the present invention.

Turning now to the figures, FIGS. 1-3, 4A and 4B illustrate an exemplary module 10. The term "module" refers to an assembly that includes hardware and software components. As shown, the module 10 includes a housing 12 and a front cover 15 (e.g., door). The housing 12 has an internal open cavity 12c (FIG. 3) for holding a container 20 (FIGS. 3-5). The front cover 15 includes at least one port 16 for transmitting fluid from the container 20 in the housing 12 out of the at least one port 16.

The module 10 is particularly suitable as a room freshener module that holds a room freshener container 20. The remainder of the application will refer to the module 10 for this use. However, the module 10 may also be used to dispense other types of substances such as, for example, insect repellant, including mosquito repellant, which may be appropriate for areas where doors are sometimes open (e.g., garages) or for open or screened in patios or decks, or locker rooms, for example.

The module 10 may include a voice command input as the input 41 or as a separate input, which may be particularly suitable for insect repellant use. The voice command inputs can include "spray now" or "OFF" so that no spray is initiated until animals or people are out of proximity. The module 10 may have a proximity detector 29 (FIG. 5) that detects for the presence of animals or people prior to initiating the dispensing. The proximity detector can include a camera, motion-detection sensor and the like.

The front cover 15 can be hingeably attached to one long side of the housing 12, as shown. The front cover 15 can be attached in other ways. For example, the front cover 15 can be attached via a hinge at the top or bottom of the housing 12 or the front cover 15 can be slidably attached to allow it to move up or down relative to the housing 12 to allow access to the cavity 12c (not shown).

As shown in FIG. 2, the port 16 can be surrounded by a wall 16w that is recessed relative to the primary body of the door 15b that surrounds the port. The wall 16w can taper to be larger as it travels outward, away from the cavity of the housing 12c.

The cover 15 can be configured to automatically close. A controller 127 (FIG. 4B, 5) in the housing 12, typically on the PCB 26, can direct the cover 15 to close upon release of any force holding the cover 15 open using a sensor for feedback on any user force holding the door open. In some embodiments, the cover 15 can be mechanically configured (e.g., spring biased) to automatically close without requiring electrical control or to release a lock that causes the mechanical structure to close the door 15.

The front cover 15 can provide a User Interface (UI) 40 including at least one input device 41 that can be configured to allow a user to manually operate the module 10 for on-demand operation of the module 10. The at least one input device 41 can also or alternatively allow a user to adjust a frequency of dispensing of the room freshener substance and/or adjust a sound level of an audible alert 42. The alert 42 can emit audible sound during and/or just prior to an active dispensing of the room freshener. The sound can be a siren or audible frequency sound and/or a verbal alert such as "stand back" dispensing in "3-2-1", for example. The UI input device 41 can be configured as a push-button, slider or rotary switch or other manual input.

The front cover 15 may include an indicator light 43, such as an LED light, which can provide color status outputs such as, for example, "green" for normal status, "yellow" or "blinking green" for low content in the container 20 status, and/or "red" for malfunction and the like. The indicator light 43 can be used to visually alert of an impending active dispensing of the room freshener.

The front cover 15 may also or alternatively include a display screen 45 (FIG. 1), such as a touch screen display or a display with a keyboard UI, for allowing a user to reset or set desired features or adjust defined features such as numbers of dispensing actions (two sprays, one spray, etc., per respective dispensing), frequency and the like.

The room freshener module 10 can include an electronic odor detector/sensor that can automatically trigger the module 10 to dispense room freshener. See, e.g., Persaud, Krishna; Dodd, George (1982). "Analysis of discrimination mechanisms in the mammalian olfactory system using a model nose". *Nature* 299 (5881): 352-5. Jin, Hye Jun; Lee, Sang Hun; Kim, Tae Hyun; Park, Juhun; Song, Hyun Seok; Park, Tai Hyun; Hong, Seunghun (2012). "Nanovesicle-based bioelectronic nose platform mimicking human olfactory signal transduction". *Biosensors and Bioelectronics* 35 (1): 335-41. The contents of these documents are hereby incorporated by reference as if recited in full herein.

In some embodiments, the housing 12 can also hold at least one actuator 50 (FIGS. 4A, 4B) that is in cooperating alignment with the room freshener container 20 to cause the room freshener container 20 to dispense room freshener through the port 16 in the cover 15.

The container 20 can hold fluid, e.g., liquid or gas and/or powder as the room freshener substance. In some particular embodiments, the container 20 is a spray canister with a nozzle 21 with a spray port 21p. The nozzle 21 can be depressed by the actuator 50 to spray fluid or powder. In other embodiments, the container 20 may be an infusion dispensing device or have a different operational configuration that does not require active spraying and/or depression of a nozzle.

Figure 4A:
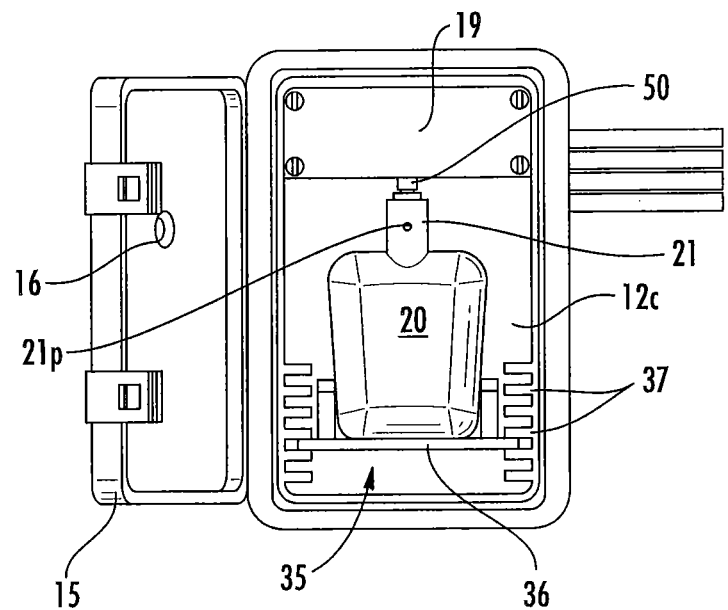
FIGS. 4A and 4B are front views of an exemplary dispensing device with the door open according to embodiments of the present invention.
Figure 4B:
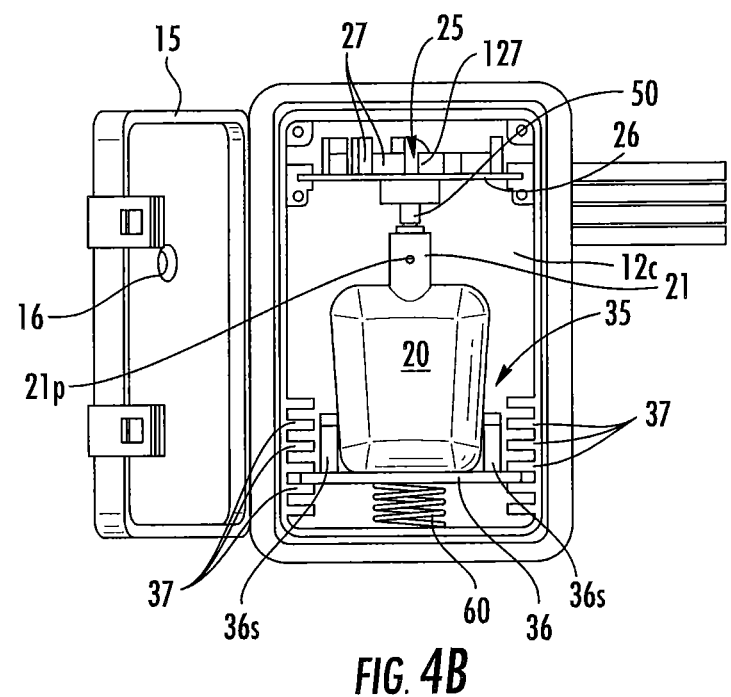
Figure 5:
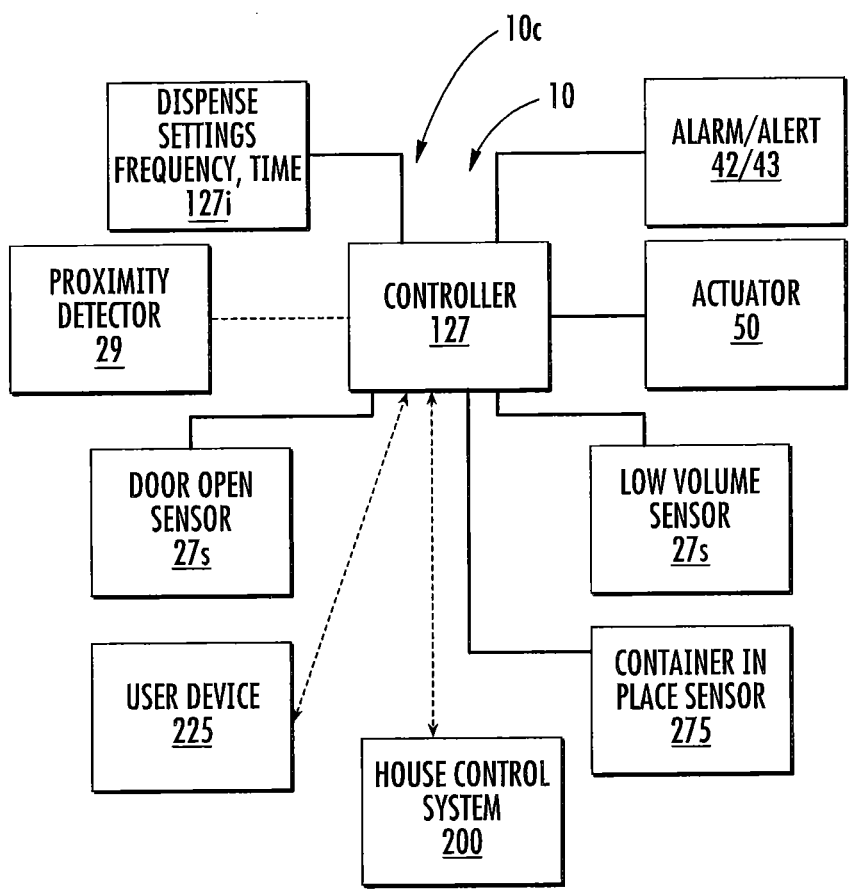
FIG. 5 is a schematic illustration of an exemplary control circuit for a dispensing module according to embodiments of the present invention.

While FIGS. 4A and 4B illustrate the container 20 in an upright orientation with the nozzle 21 above the container body, the container 20 can be used in other orientations, e.g., the reverse orientation. In still other embodiments, the nozzle 21 can be oriented to extend out of the port 16 in the cover 15 to dispense room freshener down or up relative to the cover 15, instead of straight out of the cover 15 as shown.

FIG. 4A illustrates that the housing 12 can include a printed circuit board cover 19 that can reside above the container nozzle 21 and can attach to the printed circuit board to enclose the components held above the bottom of the PCB 26. This may be a fluid-tight attachment or fluid-resistant attachment to help isolate the electrical components from undue exposure to moisture.

It is also noted that the container 20 is shown in a rigid or semi-rigid self-supporting body but flexible package containers may also be used in the module 10. If so, suitable suspension support members can be used to hold the flex-package container in position for dispensing the substance (not shown). A spring-loaded member can be used to compress the flex-package as its content is depleted (not shown).

In some embodiments, the container 20 can hold a fluid (liquid and/or pressurized gas) room freshener substance. In some embodiments, the container 20 can hold liquid room freshener. The container 20 can hold a conventional volume, such as a volume at normal use, (that is, between a 10 day-90 day supply), but other volumes are contemplated. In some embodiments, the containers 20 have a capacity of between 1 ounce and 32 ounces, typically between 2 and 16 ounces, and more typically between about 4 ounces and 12 ounces.

The container 20 can hold a substance for dispensing through the port 16 that may be odorless or have a fragrance.

The actuator 50 can be a single actuator or a plurality of actuators. The actuator 50 can be a linear and/or rotary actuator. The actuator 50 can comprise, without limitation, a solenoid, a stepper motor, a custom motor, a piezoelectric translator (transducer), a pneumatic cylinder and the like. The actuator 50 can be at any suitable location in the housing including on a sidewall, bottom, ceiling or rear wall of the housing or even on a back of the cover 15. The actuator 50 can be held a support at other locations in the housing 12.

The housing 12 can hold a printed circuit board (PCB) assembly 25 with a printed circuit board 26 and defined operational components 27 (FIG. 4B). The term "printed circuit board" is used broadly and can include flex circuits or other substrates in a single or multiple layers or components that provide defined electrical paths. Thus, the printed circuit board 26 can comprise a flex circuit with a flexible substrate body and is not required to have a rigid or semi-rigid substrate body. The components 27 can include sensors, a power supply and drive circuitry and a controller 127.

In some embodiments, the components 27 include a sensor 27s that can detect whether the cover 15 is open and suspend any active dispensing if the cover is open. A sensor 27s can be used to confirm that a container 20 is in a proper position in the housing 12. If empty or out of position, the indicator light 43 can generate the "malfunction" or "low content" visual signal. A sensor 27s can detect a presence of a container 20 before actuating the actuator 50 and/or for generating an alert to a user, for example. For the "low content" or "empty" monitoring, the sensor may detect weight or numbers of dispensing actions to "decrement" a predicted pre-defined or pre-set number of actions for a "full" container, or other appropriate parameter.

FIG. 5 is a schematic illustration of a control circuit 10c that can be totally or partially onboard the room freshener module 10. The control circuit 10c can include the controller 127 which can allow for adjustable settings 127such as dispense times, frequencies and the like. The controller 127 can communicate with the actuator 50 and/or the alarms 42, 43 (visual indicator and/or audible alert). The control circuit 10c can include various sensor inputs 27ssuch as a door open sensor 27s, low volume sensor 27s, container position sensor 27s. The controller 127 may communicate with a whole house control circuit 200 and/or a user device 225.

The module 10 can be hard wired to an electrical power circuit 300 (FIG. 9) of a building or complex, such as a recreational facility, school, hospital, nursing home, residence, hotel, motel or office building, with wires 30 as shown. The power circuit 300 can be a multi-purpose power circuit such as a conventional power circuit powering other uses such as electrical outlets, lights and the like, in a home or office.

As shown in FIG. 2, the housing 12 can include wire ports 12p in a wall thereof, e.g., typically the sidewall, but the rear wall, ceiling or floor may hold one or more of the wire ports 12p. The wires 30 can extend through the ports 12p and can include wires 30 similar to a receptacle or switch from the electrical power circuit 300 (FIG. 9), including HOT, NEUTRAL and GROUND connections and wiring. The wires 30 can be connected to the PCB assembly 25 to power the power supply and/or other components 27.

As shown in FIG. 4B, the printed circuit board (PCB) 26 can have be sized and configured to be orthogonal to the cover 15 and fit in the housing in a depth dimension as shown. However, in other embodiments, the PCB 26 can be parallel to the front cover 15 and/or reside against a side or rear wall of the housing 12. More than one printed circuit board 26 may be used for a respective room freshener module.

The module 10 can have a transceiver or transmitter-receiver for communicating over a wireless network, such as an intranet or the Internet. The module 10 can have an assigned ISP address.

Referring to FIGS. 3, 4A and 4B, the housing 12 of the room freshener module 10 can include a support member 35 such as a plate/platform 36 that can support the container 20. The housing 13 can also include an x, y, z adjustable mounting system 35 such as pairs of cooperating rails 37 that slidably receive the platform 36 to allow the platform 36 to be positioned at different vertical levels. The mounting system 35 can have lateral adjustability and depth dimension adjustability to move the container 20 in three dimensions for x, y and/or z adjustment. The platform 36 may include upwardly extending sides F to hold the container side to side and/or back to back for proper alignment with the actuator 50. The module 10 can be configured to serially cooperate with different size and/or shaped containers 20, including containers from different manufacturers and/or containers of various sizes with different volumes of room freshener.

The housing 12 of a module 10 can be configured to hold a plurality of containers 20, each in communication with a single port 16 or the cover 15 can have a plurality of ports 16, one for each container in the housing 12.

While the actuator 50 is shown residing above the container 20 in FIGS. 4 and 5, where used, an actuator 50 can be located in different locations, including under or behind the container 20.

FIG. 4B also schematically illustrates that the module 10 may include a vibration device 60 or "agitator" for shaking the container 20 to help mix the room freshener substance. The vibration device 60 can be configured to move the container side-to-side and/or up-and-down to shake the container 20. The vibration device 60 can also include an actuator such as one or more of those described above.

In some embodiments a common actuator 50/60 can be used to vibrate or agitate the container, then dispense the room freshener substance from the container 20.

The housing 12 may hold a heater such as a heating element and/or heated jacket for the container 20 to warm the container 20 to a defined temperature (not shown) for dispensing or prior to dispensing the room freshener substance from the container 20.

Figure 6A:
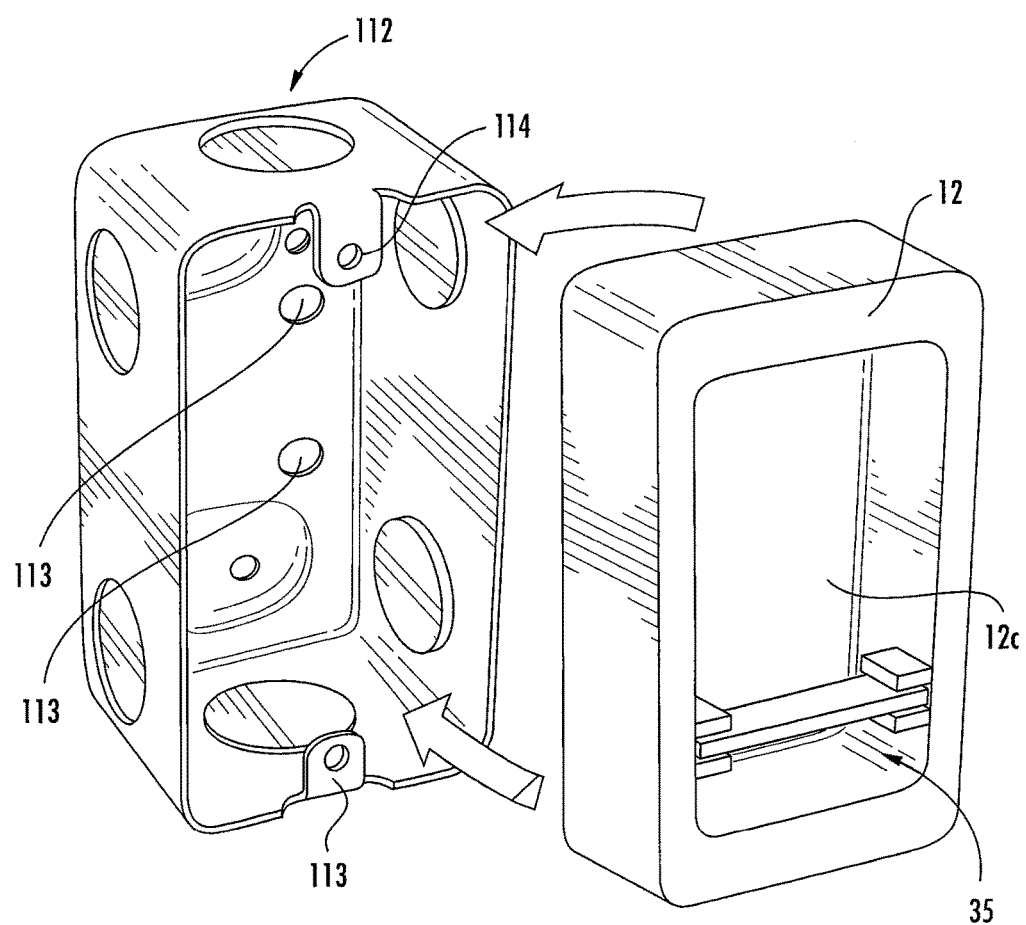
FIG. 6A is a schematic illustration of a dispensing module housing that can be held by a single gang box according to embodiments of the present invention.
Figure 6B:
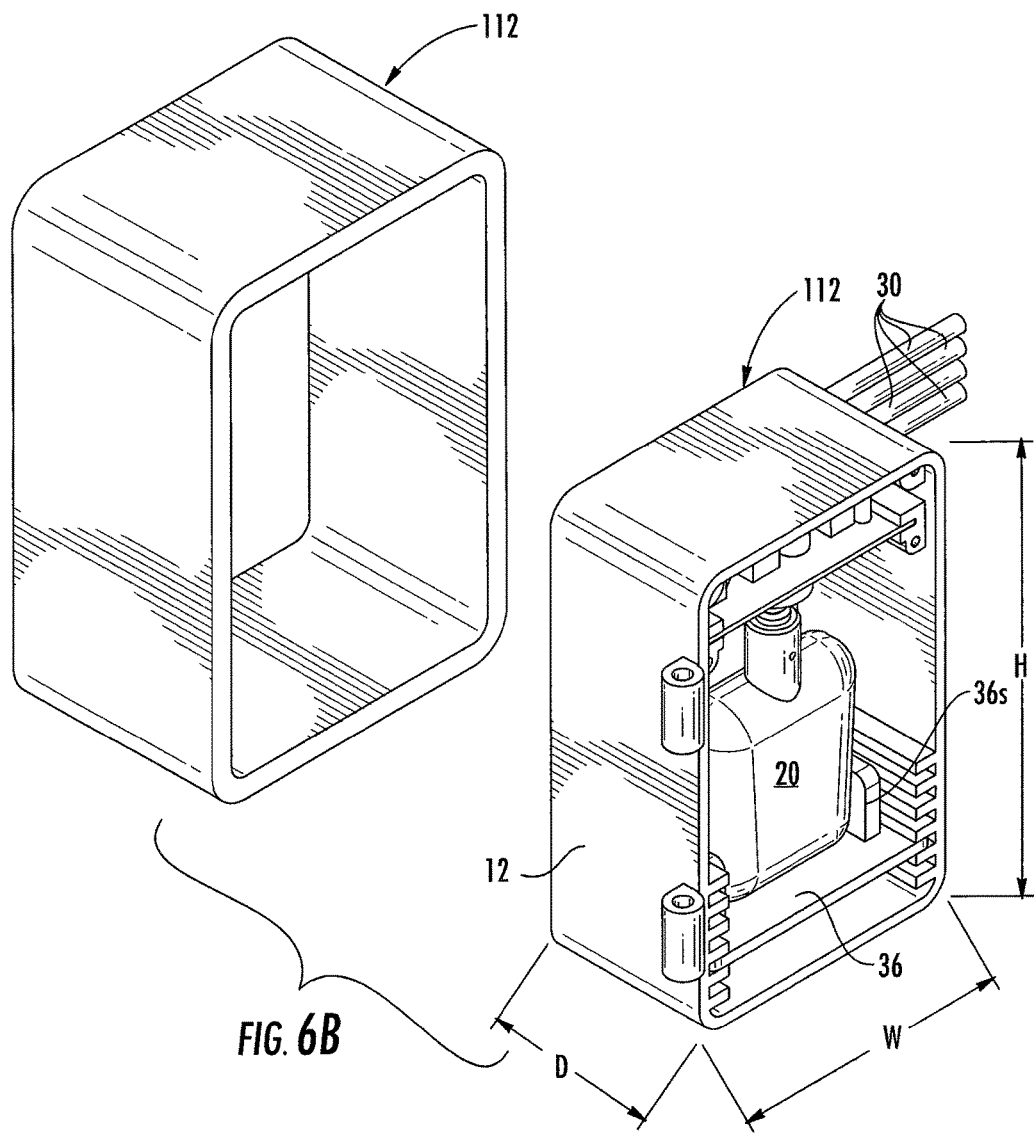
FIG. 6B is another schematic illustration of an exemplary dispensing module housing that can be held by a single gang box according to embodiments of the present invention.

As shown in FIGS. 6A and 6B, in some embodiments, the housing 12 can be configured to be held in a single gang mounting or junction box 112 for ease of installation to a wall (typically nailed or screwed to a vertical or horizontal stud via apertures 113). The wall can be an interior wall or an exterior wall and may, in some embodiments, be a wall of a room.

Thus, the housing 12 can have a depth dimension "D" that is between about 1.25 inches and about 1.75 inches, such as about 1.5 inches, or slightly smaller than a gang box depth and/or width/height. Standard single gang box depth dimensions come in 1.59 inch and 1.89 inch depths. The height and width dimensions "H" and "W", respectively can be between about 3-4 inches (H) and between about 2-2.5 inches (width), in some embodiments. The front cover 15 may attach to the gang box tabs 114 and/or to the housing 12.

Figure 7:
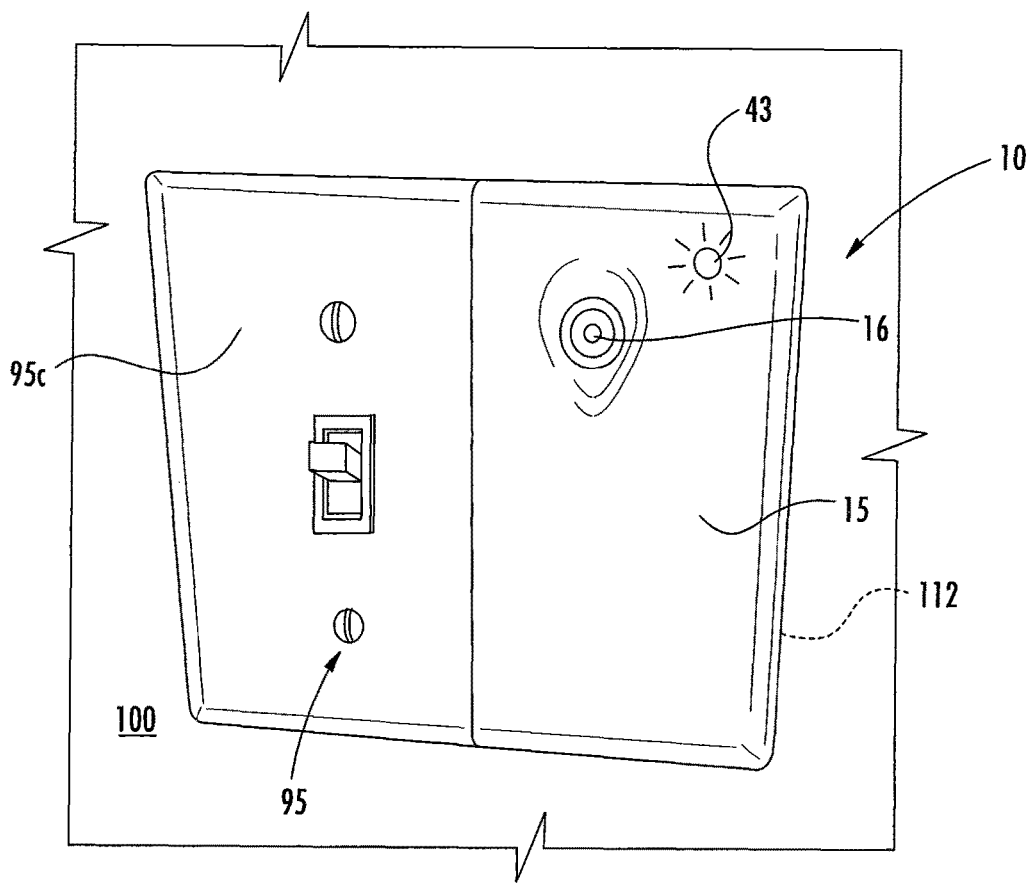
FIG. 7 illustrates an exemplary in-wall dispensing system as part of a multiple gang box configuration according to embodiments of the present invention.

As shown in FIG. 7, the housing 12 can be configured to be held in a multi-gang junction or mounting box 112 such as a double or triple gang junction box. In the embodiment shown, a light switch unit 95 (or electrical outlet unit) is held in another compartment of the multiple gang box 112.

As also shown in FIG. 7, the cover 15 can be substantially flush with the outer surface of the wall 100 in or through which the housing 12 resides and can visually have the same shape and/or surface mount appearance as a light switch wall plate 95c. The term "substantially flush" means the cover 15 resides in a plane that is parallel to and between 0.01 inches to about 0.25 inches offset from a plane of the outer surface of the wall to which the housing is mounted and/or resides within, typically similar to conventional lighting switch covers (95, FIG. 7).

In some embodiments, the housing 12 may alternatively have a custom size and is not required to be modular or standardized to fit standard gang mounting or junction boxes.

Figure 8A:
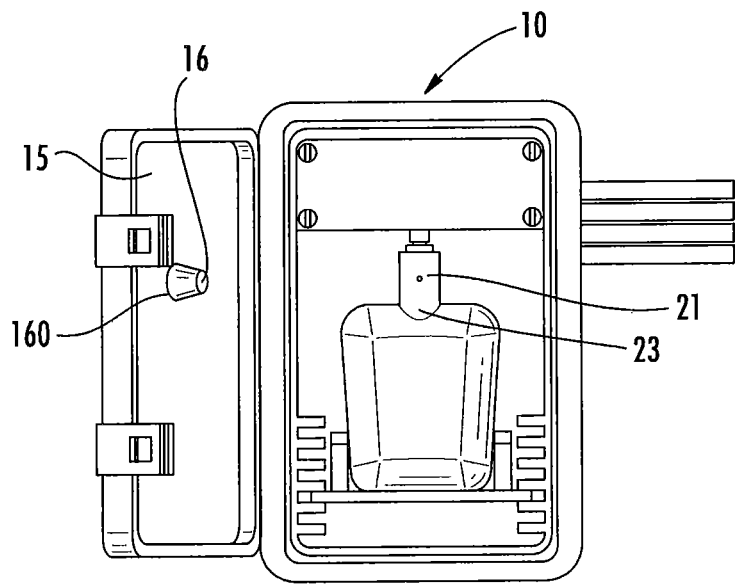
FIG. 8A is a front view of an exemplary dispensing module with an adapter used to provide a flow path according to embodiments of the present invention.
Figure 8B:
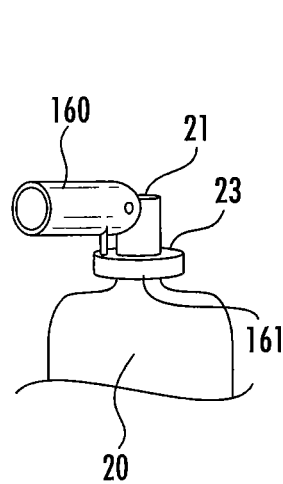
FIG. 8B is a schematic illustration of another embodiment of an adapter according to embodiments of the present invention.

FIG. 8A illustrates that the module 10 can include a flow path adapter 160 that provides an enclosed path between the container 20 and the port 16 through the door 15. The adapter 160 can be flexible or resilient to be able to compress axially when the door 15 is closed. The adapter 160 can be attached to the door 15 and may be a replaceable component. The adapter 160 may be configured with a collar 161 that can attach to the neck 23 of the container 20 as shown in FIG. 8B, for example.

Figure 8C:
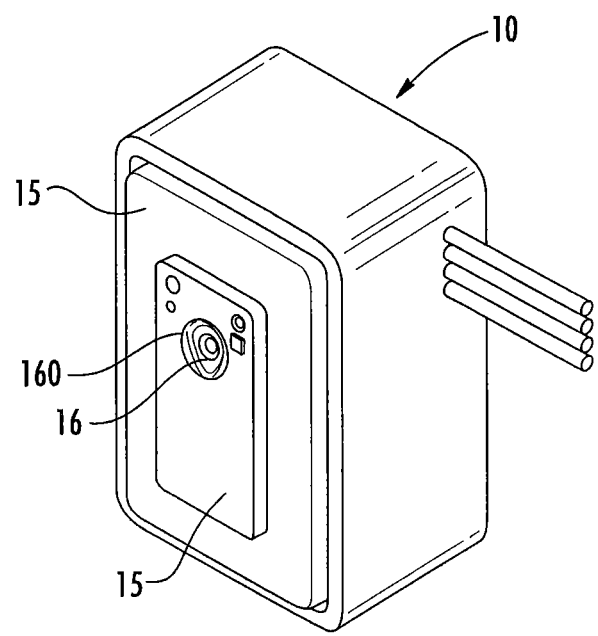
FIG. 8C is a front perspective view of a dispensing module with an adapter that can extend through the port on the front cover according to embodiments of the present invention.

FIG. 8C illustrates that the adapter 160 can extend out a distance beyond the front surface of the door 15. The adapter 160 can be elastomeric and flexible to allow a user to compress the adapter to remove or install it to the door 15. The adapter 160 may seal against the door 15, in some embodiments.

As shown in FIG. 9, the housing 12 can be held on a wall 100 of a room with a light switch adjacent a light switch unit 95 and/or electrical outlets, including Arc Fault Circuit Interrupter (AFCI) or Ground Fault Circuit Interrupter (GFCI) units. FIG. 9 also illustrates that the room freshener 10 can be mounted as a discrete unit and may be placed in any desired location, shown as below normal light switch positions.

Figure 10:
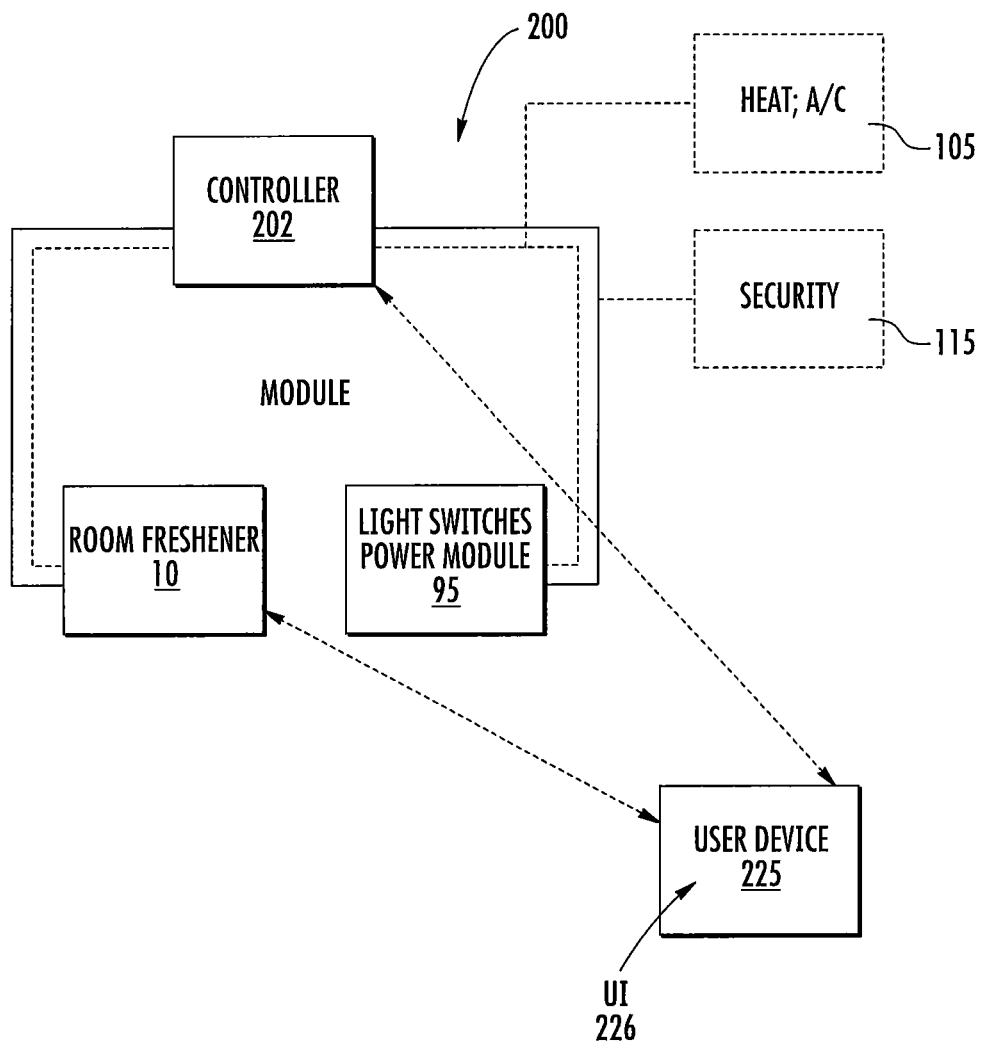
FIGS. 10 and 11 are schematic illustrations of control systems according to embodiments of the present invention.
Figure 11:
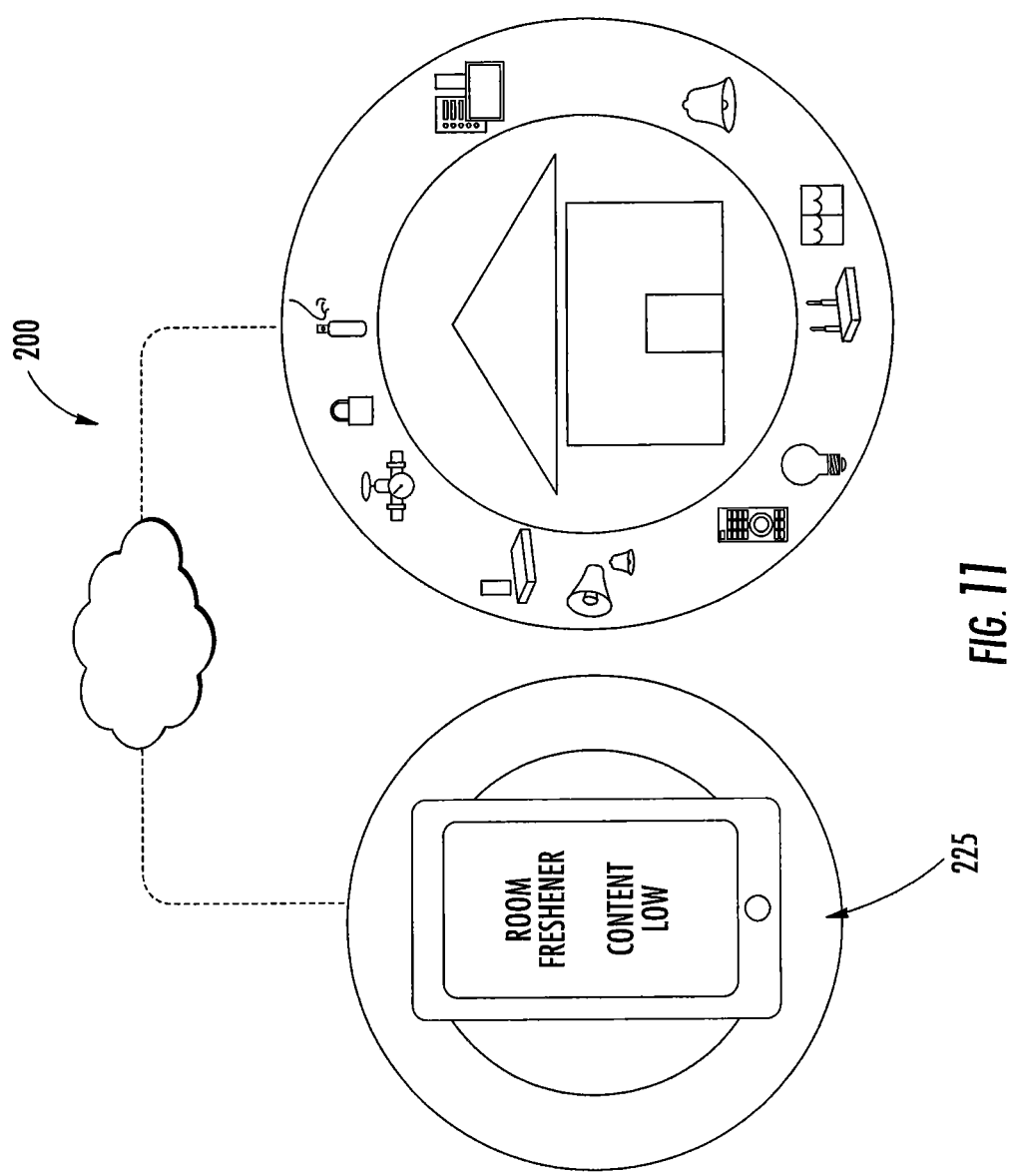

FIGS. 10 and 11 illustrate a control circuit 200 which can be a "whole house" control circuit. FIG. 10 illustrates that the control circuit 200 can have at least one primary controller 202 that directs different modules such as a lighting module 95, security module 115, and heat/A/C module 105, for adjusting/setting various operational conditions, including, for example, "ON", "OFF", and "TIME", and for the heat/A/C module "TEMPERATURE" at days, times, etc . . . The control circuit 200 can be a wireless circuit and/or may be hard-wired to one or more modules 10, 95, 105, 115. The wireless connectivity, where used, can be via BLUETOOTH®, ZIGBEE®, or Z-WAVE and the like or any wireless protocols in existence now or in the future.

The circuit 200 can also be configured to operate with a user device 225 having a User Interface (UI) 226. As shown, the user device 225 can wirelessly communicate with the controller 202 and/or with specific modules, including the room freshener module 10. The UI 226 can be a Graphic User Interface (GUI) or keypad UI or other UI that allows a user to adjust or select various operational features of the module 10. The user device 225 can be a computer, smartphone, electronic notebook, and the like. The UI 226 can be provided via an APP. The term "APP" refers to a program or piece of software designed to fulfill a particular purpose; an application, especially as downloaded by a user to a mobile device.

As shown in FIG. 11, the dispensing module 10 can be associated with a defined "spray" or "dispense" icon such as a canister and nose shown at the top of the circle of different control inputs. A similar icon/graphic can be provided as an APP for controlling the module 10.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

That which is claimed is:

1. A module comprising:
   a housing with an interior cavity, wherein the housing is sized and configured to reside internal to a wall, wherein the housing comprises wire ports on at least one of a sidewall, a rear wall, a floor or a ceiling thereof;
   a front cover attached to the housing, the front cover having at least one open port extending therethrough, wherein the front cover can be opened and closed for access to the interior cavity when the housing is mounted in the wall;
   at least one sensor and/or detector held by or in the housing configured to detect at least one of: whether a container is in position in the housing, whether the cover is closed, whether content of a container held in the housing is low, and whether an external object is in proximity to the front cover;
   an actuator in the housing; and
   a printed circuit board that holds a controller and a power supply residing in the cavity of the housing, wherein the controller is in communication with the at least one sensor and is configured to activate the actuator in the housing to dispense a substance from a container held in the housing, wherein the housing is sized and configured to reside in a single gang box, a custom size gang box, or in a space of a standard multiple gang box, and wherein wires from an electrical circuit extend through the wire ports and connect to the printed circuit board and power the power supply.

2. The module of claim 1, wherein the front cover comprises a user interface (UI) that allows a user to interact with the controller to adjust and/or set a dispensing schedule of a container held in the housing and an externally visible indicator light in communication with the controller.

3. The module of claim 1, further comprising a container with a spray nozzle held in the housing; and
a printed circuit board cover that resides behind the front cover and attaches to sidewalls of the housing and the printed circuit board to enclose components on the printed circuit board, wherein the printed circuit board is horizontally oriented and held above the spray nozzle to thereby protect electrical components from undue moisture, wherein the actuator actuates to depress the nozzle to spray the substance through the open port in the front cover, and wherein the wires are connected to an electrical distribution system of a building for the electrical circuit and extend through the wire ports at a location above the printed circuit board.

4. The module of claim 1, further comprising room freshener held in a canister with a spray nozzle, wherein the nozzle is configured to spray room freshener through the at least one port in the door of the front cover, wherein the housing further comprises a support member holding the canister in the housing in a slot formed by adjacent pairs of vertically stacked inwardly extending rails on right and left sides of the cavity, and wherein the housing further comprises a vibration member under and in communication with the support member.

5. The module of claim 1, wherein the housing comprises a container support system in the cavity, the container support system comprising spaced apart vertically stacked rails with horizontally and inwardly extending channels on left and right sides of the housing cavity that hold a support member to place a container at a desired vertical height in the cavity.

6. The module of claim 5, wherein the support member has a planar upper surface portion bounded by laterally spaced apart first and second upwardly extending sides on opposing sides thereof.

7. The module of claim 1, wherein the housing is sized and configured to reside in the single gang box.

8. The module of claim 1, wherein the printed circuit board is horizontally oriented and resides at an upper portion of the housing behind a vertically oriented cover, wherein the cover resides behind the front cover, has a smaller length than the front cover, with a bottom terminating adjacent the printed circuit board, wherein the cover is attached to the sidewalls of the housing to provide an enclosed space above the printed circuit board with the printed circuit board forming a floor of the enclosed space to thereby help isolate electrical components from undue exposure to moisture, and wherein the wire ports are above the printed circuit board.

9. The module of claim 1, further comprising a container support system in the housing cavity that allows for x, y and z positional adjustment of a respective container in the housing cavity, wherein the container support system has a base plate and the upper end of the container resides above the base in an open space in the housing aligned with the port in the front cover.

10. A room freshener module, comprising:
a housing with an interior cavity, wherein the housing is sized and configured to reside internal to a wall, and wherein the housing comprises wire ports on at least one of a sidewall, a rear wall, a floor or a ceiling thereof;
a front cover attached to the housing, the front cover having at least one open port extending therethrough, wherein the front cover can be opened and closed for access to the interior cavity when the housing is mounted to the wall, and wherein the front cover is substantially flush with an external surface of the wall;
at least one actuator in the housing cavity;
a printed circuit board assembly with a controller and power supply residing in the cavity of the housing, wherein the controller is in communication with the at least one actuator and is configured to direct the actuator to move to dispense a substance from a nozzle of a room freshener container held in the housing, and
a user interface (UI) in communication with the controller that allows a user to interact with the controller to adjust and/or set a dispensing schedule.

11. The module of claim 10, wherein the housing is sized and configured to reside in a single gang box or in a space of a multiple gang box.

12. The module of claim 10, further comprising a container of room freshener held in the housing cavity with the nozzle in alignment with the open port of the front cover, wherein the printed circuit board assembly comprises a printed circuit board held above the nozzle in the cavity of the housing, and wherein the printed circuit board provides a floor of an enclosure space above the nozzle with a printed circuit board cover attached to sidewalls of the housing behind the front cover and above the nozzle.

13. The module of claim 10, further comprising an LED indicator light in communication with the controller and an audible alert in communication with the controller, wherein the printed circuit board assembly comprises a printed circuit board held above the nozzle in the cavity of the housing with a printed circuit board cover also held above the nozzle in the cavity of the housing.

14. The module of claim 10, wherein hot, ground and neutral wires from an electrical circuit extend through the wire ports in the housing to be hard wired to the printed circuit board assembly to power the power supply, and wherein the wire ports reside above the printed circuit board and both the printed circuit board and the wire ports are in an upper portion of the housing.

15. The module of claim 10, wherein the controller is in communication with a whole house control circuit that also controls other household devices including one or more of a security alarm system, a lighting system and/or a heating and air conditioning system.

16. A system for dispensing a substance to an environment, comprising:
a housing that resides internal to a wall, the housing having right and left sidewalls, a back, a ceiling and a floor that form a rectangular interior cavity closed by a rectangular front cover pivotably held by one sidewall of the housing so that front cover is flush or substantially flush with the wall, wherein the front cover has at least one open port extending therethrough, and wherein the front cover can be pivotably opened and closed for access to the interior cavity when the housing is mounted in the wall;

at least one actuator held in the housing;

at least one sensor held in the housing configured to detect at least one of: whether a container is in position in the housing, whether the cover is closed, or whether content of a container held in the housing is low;

a printed circuit board assembly comprising a controller and a power supply residing in the cavity of the housing, wherein the controller is in communication with the at least one sensor and the at least one actuator and is configured to direct the actuator to depress a nozzle of a container in the housing to dispense a substance from the container in the housing; and hot, ground and neutral wires from an electrical circuit hard wired to the printed circuit board assembly to power the power supply.

17. The system of claim 16, wherein the housing is sized and configured to reside in a single gang box or in a space of a multiple gang box.

18. The system of claim 16, further comprising a container of room freshener held in the housing cavity with nozzle in alignment with the open port of the front cover, wherein the front cover resides adjacent to a light switch with a co-planar front surface.

19. The system of claim 16, wherein the front cover comprises an LED indicator light in communication with the controller, wherein the system further comprises an audible alert in communication with the controller, and wherein the printed circuit board assembly comprises a printed circuit board held above the nozzle in the cavity of the housing with a printed circuit board cover also held above the nozzle in the cavity of the housing.

20. The system of claim 16, wherein the controller is in communication with a whole house control circuit that also controls other household devices including one or more of a security alarm system, a lighting system and/or a heating and air conditioning system.

21. The system of claim 10, wherein the front cover resides laterally spaced apart from and adjacent to a light switch with a co-planar front surface.

22. The system of claim 1, wherein the front cover is coplanar with the wall, wherein the printed circuit board is horizontally oriented and resides at an upper portion of the housing behind a vertically oriented printed circuit board cover that is behind the front cover and has a smaller length than the front cover, and wherein the printed circuit board cover is attached to the printed circuit board and sidewalls of the housing to provide an enclosed space above the printed circuit board to thereby help isolate electrical components from undue exposure to moisture.

23. The system of claim 1, further comprising a flow path adapter that is axially compressible and provides an enclosed flow path between the container in the housing and the port in the front cover.

24. The module of claim 10, further comprising a flow path adapter that is axially compressible and provides an enclosed flow path between the nozzle of the container in the housing and the port in the front cover.

* * * * *